United States Patent
Boyer et al.

(10) Patent No.: US 6,693,225 B2
(45) Date of Patent: Feb. 17, 2004

(54) PROCESS FOR HYDROGENATING CUTS CONTAINING HYDROCARBONS, IN PARTICULAR UNSATURATED MOLECULES CONTAINING AT LEAST TWO DOUBLE BONDS OR AT LEAST ONE TRIPLE BOND

(75) Inventors: Christophe Boyer, Charly (FR); Vincent Coupard, Lyons (FR); Quentin Debuisschert, Rueil-Malmaison (FR)

(73) Assignee: Institut Francais du Petrole, Ruiel Mal Maison Cedex (FR)

( * ) Notice: Subject to any disclaimer, the term of this patent is extended or adjusted under 35 U.S.C. 154(b) by 0 days.

(21) Appl. No.: 09/892,764

(22) Filed: Jun. 28, 2001

(65) Prior Publication Data

US 2002/0022754 A1 Feb. 21, 2002

(30) Foreign Application Priority Data

Jun. 28, 2000 (FR) .............................. 00 08358

(51) Int. Cl.$^7$ .............................. C07C 5/02; C07C 5/05; C07C 5/08; C07C 5/03
(52) U.S. Cl. ....................... 585/265; 585/258; 585/271; 585/273; 585/275; 585/259; 208/144
(58) Field of Search ................................. 585/265, 258, 585/259, 271, 273, 275; 208/144

(56) References Cited

U.S. PATENT DOCUMENTS

| | | | |
|---|---|---|---|
| 4,113,603 A | 9/1978 | Bauer | 208/89 |
| 4,469,907 A | 9/1984 | Araki et al. | 585/259 |
| 4,704,492 A | 11/1987 | Nemet-Mavrodin | 585/259 |
| 4,960,960 A | 10/1990 | Harrison et al. | 568/881 |

FOREIGN PATENT DOCUMENTS

| | | |
|---|---|---|
| EP | 2 450 867 | 10/1980 |
| EP | 0 523 482 A2 | 1/1993 |
| EP | 0 700 984 A2 | 3/1996 |

*Primary Examiner*—Bekir L. Yildirim
(74) *Attorney, Agent, or Firm*—Millen, White, Zelano & Branigan, P.C.

(57) ABSTRACT

Hydrogenation of a liquid cut containing hydrocarbons, in particular unsaturated molecules containing at least two double bonds or at least one triple bond, is described wherein the unsaturated molecules are at least partially hydrogenated to less unsaturated molecules containing at least one double bond, in at least one reactor comprising at least two distinct beds of at least one hydrogenation catalyst, and wherein a gas phase containing hydrogen is introduced, a portion thereof being mixed with said cut upstream of the first catalyst bed and a portion thereof being introduced upstream of the subsequent beds contained in said reactor.

18 Claims, 4 Drawing Sheets

Figure 1:
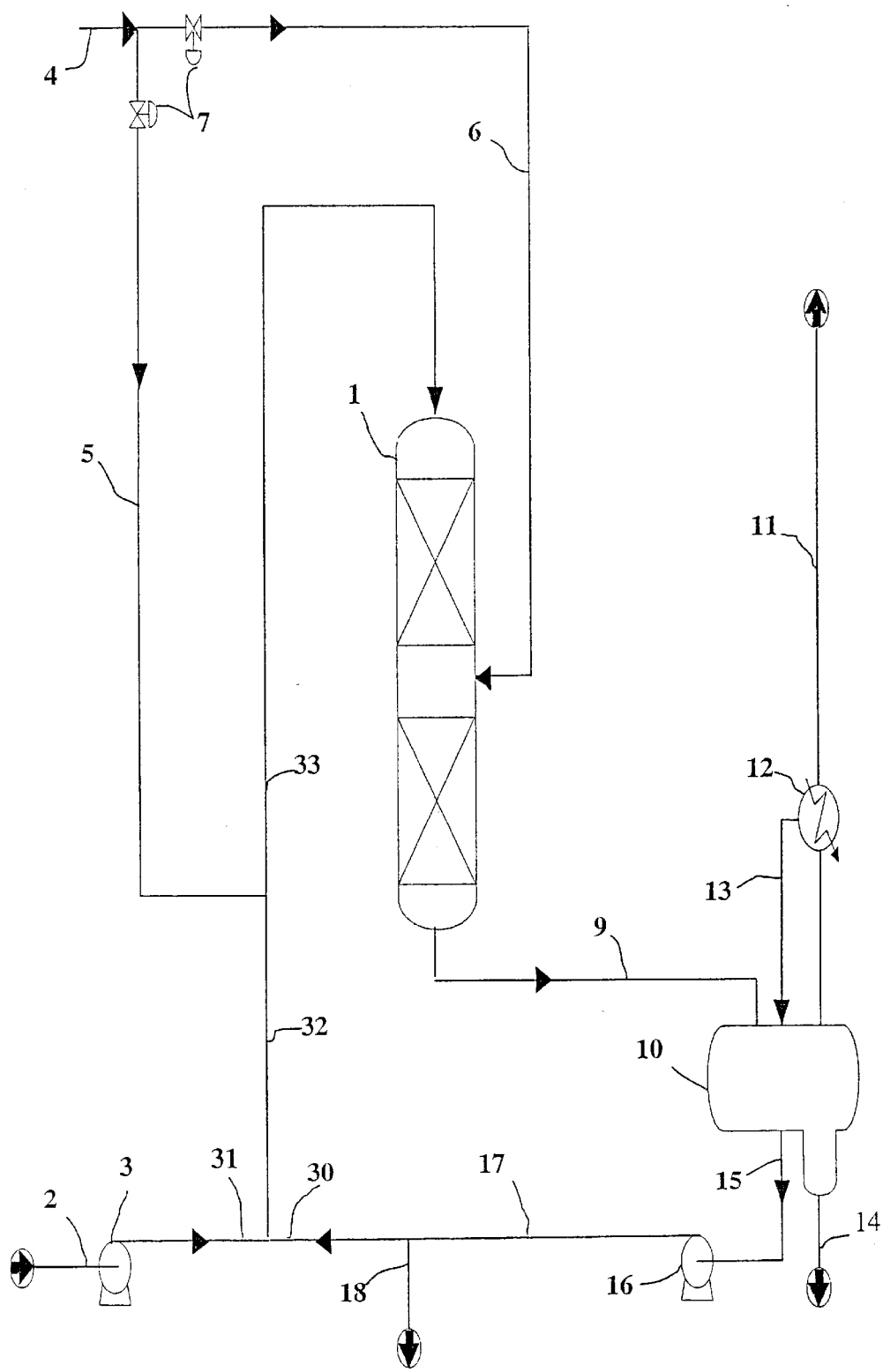

PROCESS FOR HYDROGENATING CUTS CONTAINING HYDROCARBONS, IN PARTICULAR UNSATURATED MOLECULES CONTAINING AT LEAST TWO DOUBLE BONDS OR AT LEAST ONE TRIPLE BOND

SUBJECT MATTER OF THE INVENTION

The present invention proposes a process for hydrogenating a cut containing hydrocarbons comprising highly unsaturated molecules containing at least two double bonds or at least one triple bond such as hydrocarbon molecules, for example 1,3-butadiene, 1,2-butadiene, vinyl acetylene and hydrocarbon molecules containing 4 or more carbon atoms such as 1-butene, 2-butene, n-butane, isobutane and/or isobutene. More particularly, this process is applicable to hydrogenating cuts containing hydrocarbons, in particular butadiene. The reaction can be controlled to produce a high selectivity for butene in the product without losing isobutene and minimising complete hydrogenation of the butenes to butane. Four particular implementations are proposed for the process of the invention: the first and second have a very good selectivity for butene with a lower butadiene conversion (between 80% and 100%); the third and fourth can achieve a butadiene conversion of close to 100%.

PRIOR ART

International patent WO-A-93/21137, corresponding to U.S. Pat. No. 5,281,753, proposes a process for selective hydrogenation and simultaneous isomerisation of hydrocarbons in a mixture containing unsaturated molecules (in particular di-olefins) and containing 4 or more carbon atoms. Hydrogenation is carried out in the presence of gaseous hydrogen through a catalytic reactor with fixed beds. The hydrogen is introduced into the reactor through at least three successive points, gradually increasing the mole ratio of hydrogen to the fraction of unsaturated molecules. That patent teaches that such a ratio should be increased from a sub-stoichiometric ratio at the first injection point to a stoichiometric ratio at the second point, and finally to a ratio that is in excess with respect to the stoichiometry at the last injection point. One particular application described in that patent concerns hydrogenating butadiene in a hydrocarbon cut also containing butane and butenes. That patent teaches that the catalytic beds are separated from each other by beds of inert materials and hydrogenation is carried out as described, for example, in the flow chart of FIG. 1 in feed and hydrogen upflow mode. No mention is made of recycling a portion of the hydrogenated product and similarly, the excess of hydrogen introduced in particular to the third bed is not specified.

U.S. Pat. No. 3,764,633 describes a process for isomerising mono-olefins containing a double bond disposed at the end of a molecule containing at least 4 carbon atoms and selective simultaneous hydrogenation of polyunsaturated compounds such as di-olefins or acetylenic compounds contained in the treated hydrocarbon cut. That patent teaches that the process can use a plurality of successive beds. In that case, hydrogen injection is staged between the different beds, but the total proportion of hydrogen injected into the first bed is in the range 75% to 98%. The hydrogen is preferably introduced with the feed after vaporising that feed. The quantity of hydrogen introduced decreases from the first catalyst bed to the last catalyst bed. Each reactor contains, for example, two beds of catalyst separated by a partition, the hydrogen being introduced upstream of each of the beds and into each bed. The effluent containing the hydrocarbons and hydrogen leaving the first bed is not sent directly to the second bed but leaves the reactor and passes into a heat exchanger before being re-introduced into the reactor beneath the partition separating the beds above said second bed. That patent does not teach recycling a fraction of the hydrogenated product and further, when one reactor is operating, the other is in a catalyst regeneration phase.

U.S. Pat. No. 4,260,840 concerns selective hydrogenation of butadiene in a C4 cut. The product contains at least 30% by weight of 1-butene and butadiene in trace amounts. That feed is hydrogenated to minimise 1-butene isomerisation and to minimise hydrogenation of the butenes to butane. No mention is made of staged injection of hydrogen nor of recycling a fraction of the hydrogenated product.

U.S. Pat. No. 4,960,960 describes a process for selective hydrogenation containing two zones that may comprise one bed or two successive beds each possibly being supplied with gaseous feed. That process is not specific to a particular hydrogenation reaction and that patent does not teach the staged introduction of hydrogen upstream of each of the catalyst beds. Finally, that patent teaches that the liquid phase passes into a static distributor contained in the reactor itself, hydrogen arriving via another inlet above that static distributor, and no mention is made of the possibility of using a static mixer to improve mixing of the gaseous hydrogen-containing phase and the liquid hydrocarbon-containing cut.

U.S. Pat. No. 4,469,907, having the same priority as European patent application EP-A-0 087 980, describes a method for hydrogenating a petroleum cut containing unsaturated molecules containing 4 or more carbon atoms using a fixed bed reactor in which hydrogen is injected at 2 or 3 successive points. The authors state that the quantity of hydrogen injected into the 2 or 3 injection point corresponds to a fraction in the range 5% to 100% of the quantity injected at the preceding point. The excess hydrogen over the stoichiometry is in the range 10% to 100%. The conversion or selectivity performance is not specified. That patent does not teach recycling a portion of the hydrogenated product from the first reactor.

EP-A-0 523 482 describes a process for selective hydrogenation of butadiene in the liquid phase alone or in a trickle flow. The treated petroleum feeds contain between 20% and 80% of butadiene. The process comprises two reaction sections: at the outlet from the first zone, the butadiene residue in the product is in the range 0.1% to 20% by weight and at the outlet from the second zone it is in the range 0.005% to 1% by weight. In general, the patent envisages a ratio of 5 between the amount of butadiene at the outlet from the first zone and the amount at the outlet from the second zone. That patent envisages a selectivity for butenes of more than 96%. The operating conditions are: a temperature of 40° C. to 120° C., a pressure of 5 to 50 bars and an hourly space velocity of 0.1 to 30 h$^{-1}$. No mention is made of staged injection of hydrogen into the reactor. That patent teaches recycling a portion of the hydrogenated product and using two separate reactors in series with a quantity of hydrogen supplied to each of the two zones of once to twice the necessary stoichiometric quantity. It does not teach the possibility of recycling a portion of the product leaving the first reactor overhead. The quantity of hydrogenated product that is recycled is not mentioned.

EP-A-0 700 984 describes a process for hydrogenating a hydrocarbon cut containing 2 to 20 carbon atoms containing mono-unsaturated hydrocarbons and at least one polyunsaturated hydrocarbon. The feed to be treated is at least partially in the liquid form and circulates through a reactor containing at least one fixed bed and at least one static mixer located upstream of the outlet section. That patent states that the beds can be staged in the same reactor with the possibility of injecting hydrogen between two beds. Partial recycling of the product can optionally be carried out, but the quantity of recycled product is not defined. Further, that patent does not teach the use of two successive reactors each comprising two catalyst beds, nor in that case recycling a portion of the liquid product from the first reactor obtained after separating out a gas phase and eliminating the aqueous phase it contains.

DESCRIPTION OF THE INVENTION

In its broadest aspect, the present invention concerns a process for hydrogenating a liquid cut containing hydrocarbons and in particular unsaturated molecules containing at least two double bonds or at least one triple bond wherein the unsaturated molecules containing at least two double bonds or at least one triple bond, are at least partially hydrogenated into less unsaturated molecules containing at least one double bond, in at least one reactor comprising at least two distinct beds of at least one hydrogenation catalyst, and wherein a portion of a gas phase containing hydrogen is introduced as a mixture with said cut upstream of the first catalyst bed and a portion thereof is introduced upstream of the subsequent beds contained is said reactor, and wherein in the first reactor, hydrogenation is carried out in a liquid and gas downflow mode and wherein the gas/liquid mixture from said first reactor is sent to a separation section from which a gas phase is recovered, an aqueous phase is eliminated and a liquid phase is recovered containing the hydrogenated product from said first reactor, at least a portion of which is returned as a mixture with said cut to the inlet to said first reactor upstream of the first catalyst bed contained in said first reactor.

In particular, the invention is applicable to hydrogenating a cut containing hydrocarbons which is a cut essentially containing hydrocarbons and which contains butadiene. Within the context of the present invention, the term "essentially" means that the cut contains at least 80%, normally at least 95% and usually at least 98% by weight of hydrocarbons with respect to the total weight of the cut.

The invention is of particular application to the selective hydrogenation of a butadiene-rich petroleum cut i.e., the hydrocarbon feed to be treated generally contains between about 20% and about 95% by weight of butadiene, normally in the range 25% to 75% by weight of butadiene and preferably in the range 30% to 50% by weight of butadiene. This hydrogenation can be carried out with a flooded gas-liquid flow regime with a volume boil-off rate in the range 5% to 30%, preferably in the range 5% to 20%, or in liquid flow alone, with a boil-off rate in the range 0 to 5%. Preferably, the reaction is carried out in liquid alone. The process of the present invention is normally carried out in at least one fixed bed reactor, preferably in 1 or 2 reactors. Each reactor contains at least two superimposed beds, preferably 2 to 4 beds, more preferably 2 beds, independently supplied with gaseous feed. The recycle ratio of the liquid phase containing the hydrogenated product from the first reactor to said first reactor, equal to the ratio of the volume flow rate of the recycle to the volume flow rate of the feed entering said reactor, is about 10:1 to about 30:1, normally in the range 15:1 to 25:1.

The first reactor contains two successive beds of catalyst and the distribution of the flow rate of the hydrogen-containing gas phase injected as a mixture with the liquid cut into the head of said first reactor upstream of the first catalyst bed is about 50 mole % to about 70 mole % with respect to the sum of the total molar flow rate of the gas phase injected into the reactor. More precisely, the first reactor contains two superimposed beds of catalyst and the distribution of the flow rate of the gas feed injected into the first reactor between the inlet line and the secondary injection line is in the range about 50 mole % to about 70 mole % with respect to the total molar flow rate injected into the reactor for the inlet line, and, in the range 30 mole % to 50 mole % with respect to the total molar flow rate injected into the reactor for the secondary injection line upstream of the second catalyst bed. At the level of injection of the gas phase to the head of the reactor, the molar proportion of hydrogen is less than the stoichiometry compared with all of the polyunsaturated C4 compounds comprising at least one triple bond and/or at least 2 double bonds, this proportion being in the range 0.5 to 1 mole of hydrogen per mole of polyunsaturated C4 compound to be treated. After secondary injection, the molar proportion of hydrogen is higher than the stoichiometry with respect to all of the polyunsaturated C4 compounds containing at least one triple bond and/or at least 2 double bonds, this excess over the stoichiometry preferably being in the range 1% to 30% and more preferably in the range 1% to 20%. In a particular implementation of the invention, the liquid feed and gas phase introduced into the head of the first reactor traverse a static mixer upstream of said introduction into said reactor.

In a particular implementation, the gas phase from the separation section is sent to a chilling section from which a liquid phase is recovered and recycled to the separation section.

The pressure at the reactor inlet is generally in the range 1 to 3 MPa, usually in the range 2 to 2.5 MPa. The temperature at the reactor inlet is generally in the range 30° C. to 60° C., preferably in the range 35° C. to 45° C. The hourly space velocity, calculated with respect to the inlet feed flow rate, is generally in the range 3 to 10 $h^{-1}$ (expressed as $m^3$ at 15° C. of liquid feed to be treated per $m^3$ of catalyst per hour), preferably in the range 3.5 to 7.5 $h^{-1}$.

The hydrogenation catalysts used are identical or different in each catalytic bed of each reactor and preferably comprise, on a mineral support, at least one noble group VIII metal, more preferably palladium on alumina.

Highly preferably, the catalyst used in the first reactor contains 0.2% by weight of palladium usually associated with one or more dopants which can, for example, be selected from the group formed by gold, silver and copper, in a quantity generally of about 1 to about 10000 ppm by weight, normally about 1 to 5000 ppm by weight and usually about 1 to about 1000 ppm by weight, preferably on a high purity alumina support. This first reactor preferably contains two beds of identical catalyst (same noble metal, same quantity of noble metal and the same support). When two reactors are used in series, the catalyst used in the second reactor normally contains a larger quantity of noble metal than the catalyst contained in the catalytic beds of the first reactor. As an example, this catalyst contains 0.3% by weight of palladium, preferably on a high purity alumina support. The gaseous feed is normally composed of a mixture of hydrogen and at least one second gas that is inert for the reaction; this second gas can, for example, be selected in the group consisting of methane, propane, butane, nitrogen, argon, carbon monoxide and carbon dioxide. This second gas is generally mainly methane or propane. The molar proportion of hydrogen in the gas feed is generally in the range 60% to 99.99%, usually in the range 80% to 99.99%, the complement to 100% being one of the inert gases cited above.

The performances of the process combining a single reactor can produce a butadiene content at the outlet from reactor (1) that is normally in the range 0.1% to 5% by weight. The selectivity 7 for butenes in the reaction of hydrogen on butadiene (defined by equation (1) below) is generally in the range 90% to 100%, usually in the range 95% to 100%. The butadiene conversion between the inlet to the reactor and its outlet is generally in the range 70% to 100%.

$$\eta = \frac{\sum \text{butenes}_{outlet} - \sum \text{butenes}_{inlet}}{\text{butadiene}_{inlet} - \text{butadiene}_{outlet}} \quad (1)$$

The process of the present invention can integrate a second reactor in series with the first reactor the characteristics of which were described in the previous paragraph. In the case where this second reactor contains two successive (superimposed) beds, the flow rate of the gas injected upstream of the first bed is generally in the range 50% to 70% of the total molar flow rate injected into said second reactor and the gas flow rate injected upstream of the second bed of said second reactor is generally in the range 30% to 50% of the total molar flow rate injected into said second reactor and usually, this distribution is 50% and 50% for the two injection points. At the level for injection of the gas phase into the inlet to the second reactor (upstream of the first bed of catalyst contained in said second reactor), the molar proportion of hydrogen is preferably less than or equal to the stoichiometry with respect to all of the polyunsaturated C4 compounds comprising at least one triple bond and/or at least two double bonds: this proportion is in the range 0.5 to 1 mole of hydrogen per mole of polyunsaturated C4 compound to be treated. At the level of the secondary injection, upstream of the second bed, the molar proportion of hydrogen is preferably higher than the stoichiometry with respect to all of the polyunsaturated C4 compounds comprising at least one triple bond and/or at least 2 double bonds: this excess is preferably in the range 10% to 200%, more preferably in the range 30% to 150%. The temperature at the reactor inlet is generally in the range 30° C. to 60° C., preferably in the range 35° C. to 45° C. The hourly space velocity, calculated with respect to the flow rate of the feed at the inlet, is generally in the range 3 to 10 h–1, preferably in the range 4.5 to 7.5 h$^{-1}$. The performances of this process, comprising two reactors in series, allow to produce a butadiene content generally in the range 0.1% to 5% by weight at the outlet from the first reactor and the final product from the second reactor generally has a butadiene content in the range 10 ppm to 1% by weight. The butene selectivity η in the reaction of hydrogen on butadiene is generally in the range 90% to 100% at the outlet from the first reactor and in the range 95% to 100% at the outlet from the second reactor. Butadiene conversion is generally in the range 95% to 100% over the whole of the process. Usually, when hydrogenation is carried out in two successive reactors, the first one operates in liquid and gas downflow mode while the second operates in liquid and gas upflow mode and each of said reactors comprises:

at least two successive beds of catalyst;
an introduction upstream of each of the catalyst beds of a gas phase containing hydrogen corresponding to a portion of the total gas phase introduced into said reactors;

an introduction of a liquid phase corresponding to a portion of the hydrogenated product from said first reactor.

The accompanying figures show non-limiting flow diagrams for implementing the process of the invention.

DESCRIPTION OF FIG. 1

The flowchart comprises a fixed bed reactor (1). This reactor (1) is a fixed bed reactor with two superimposed beds that operate in co-current downflow mode. The liquid feed (2) is injected via a pump (3) at the head of the reactor via lines (31), (32) and (33). The gaseous feed (4) is injected at two levels upstream of reactor (1): at the level of the line for injecting liquid feed via lines (5) and (33) and at the intermediate level of the reactor, between two successive beds via line (6). The distribution of the flow rates for gas injection between line (5) and line (6) is controlled using two regulating valves (7) This mixture can optionally traverse a heat exchanger either at startup or throughout the operation of the unit (exchanger mounted as a by-pass with respect to the principal inlet line, not shown in FIG. 1). At the outlet from reactor (1), the gas/liquid mixture from the reactor is injected via line (9) into a high pressure separator (10). The gaseous effluents (11) from separator (10) then traverse a condenser (12) to recover the compounds of the C4 cut contained in the gas phase as a liquid phase (after condensing). This condensed phase then regains the separator via line (13). The aqueous fraction is evacuated at (14) from the lower portion of the separator. In the lower intermediate portion, the liquid effluent (15) is returned through a recycle pump (16) to the inlet to reactor (1) via lines (17), (30), (32) and (33). A fraction of this recycle flow is diverted into line (18) to constitute the reaction product.

DESCRIPTION OF FIG. 2

The flowchart is identical to that shown in FIG. 1, with the exception that upstream of the head of the reactor, the gas/liquid mixture (line (33)) traverses a static mixer (8) of the same type as that described in EP-A-0 700 984.

DESCRIPTION OF FIG. 3

This flowchart comprises a first fixed bed reactor (1) that contains two superimposed beds and which functions in co-current (gas-liquid) downflow mode. The second reactor (19) is a fixed bed reactor with two superimposed beds functioning in upflow mode. The liquid feed (2) is injected through a pump (3) into the head of reactor (1) via lines (31), (32) and (33). The gaseous feed (4) is injected at two levels upstream of reactor (1): at the level of the line for injecting liquid feed via lines (5) and (33) and at the intermediate level of the reactor, between two successive beds via line (6). The distribution of the flow rates of the gas injection between line (5) and line (6) is controlled using two regulating valves (7). This mixture can traverse a heat exchanger either at startup or throughout the operation of the unit (exchanger mounted as a by-pass with respect to the main inlet line, not shown in FIG. 3). At the outlet from reactor (1), the gas/liquid mixture from the reactor is injected via line (9) into a high pressure separator (10). The gaseous effluents (11) from the separator (10) then traverse a condenser (12) to recover the compounds of the C4 cut contained in the gas phase as a liquid phase (after condensing). This condensed phase then regains the separator via line (13). The aqueous fraction is evacuated via (14) from the lower portion of the separator. In the lower intermediate portion, the liquid effluent (15) is returned via a recycle pump (16) to the inlet to reactor (1) via lines (17), (30), (32) and (33). A fraction of this recycle is diverted into line (18) to supply reactor (19).

In reactor (19), the liquid feed is injected into the lower portion of the reactor and the gaseous feed, with the same composition as that injected into reactor (1), is injected at two levels: upstream of the first bed via lines (34) and (20) and upstream of the second bed via lines (34) and (21). The distribution of the gaseous flow rates injected at (20) and (21) is controlled by two regulating valves (22). At the outlet from reactor (19), the effluent is recovered via line (23) and traverses a means (24) intended to separate the lightest fraction of the products leaving said means via line (25) (C1 to C3 cut and hydrogen) which rejoins the gaseous effluents from separator drum (10) in line (11). The liquid phase constitutes the reaction product and is recovered via line (26).

DESCRIPTION OF FIG. 4

Figure 3:
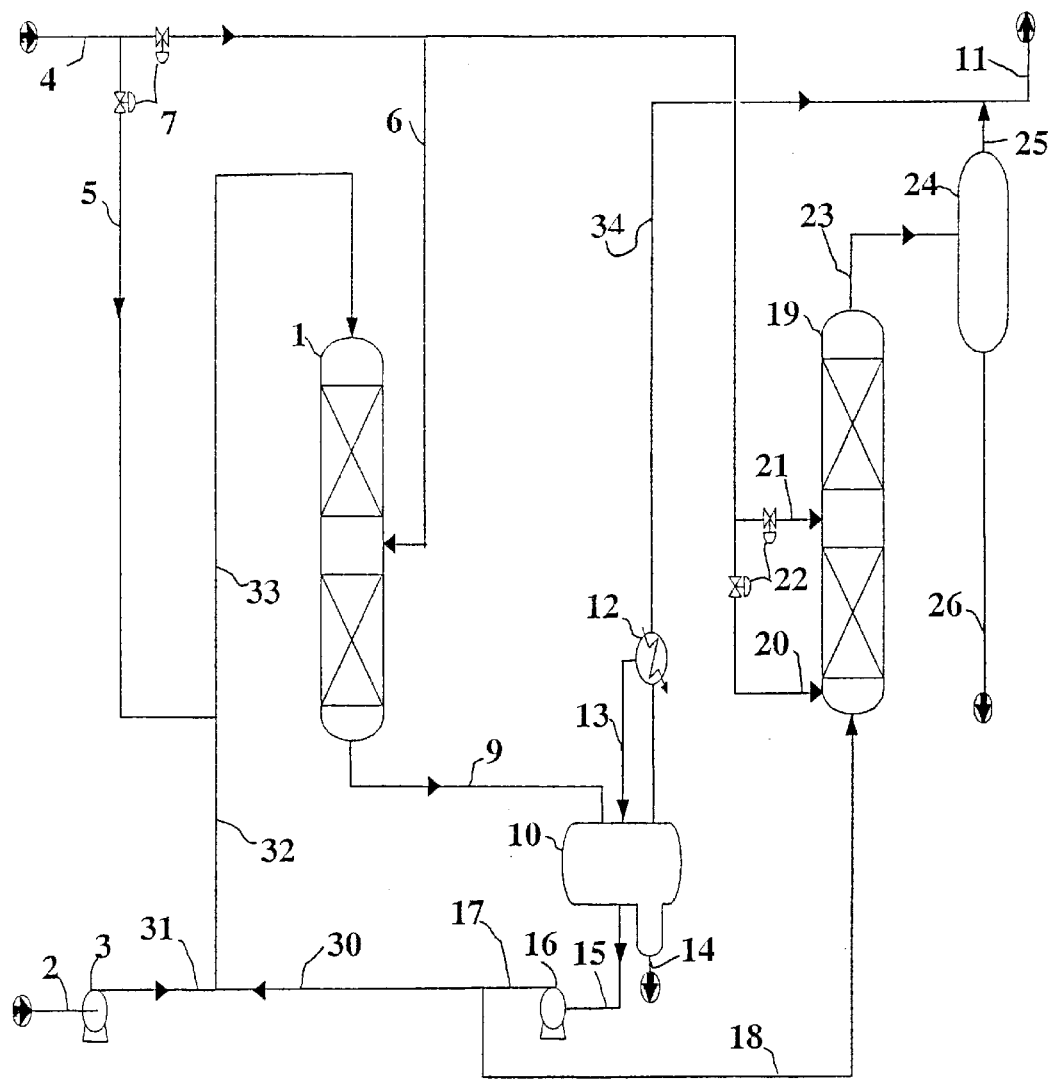

The flowchart is identical to that shown in FIG. 3, with the exception that upstream of the head of the reactor, the gas/liquid mixture (line (33)) traverses a static mixer (8) of the same type as that described in EP-A-0 700 984.

EXAMPLE 1

Figure 2:
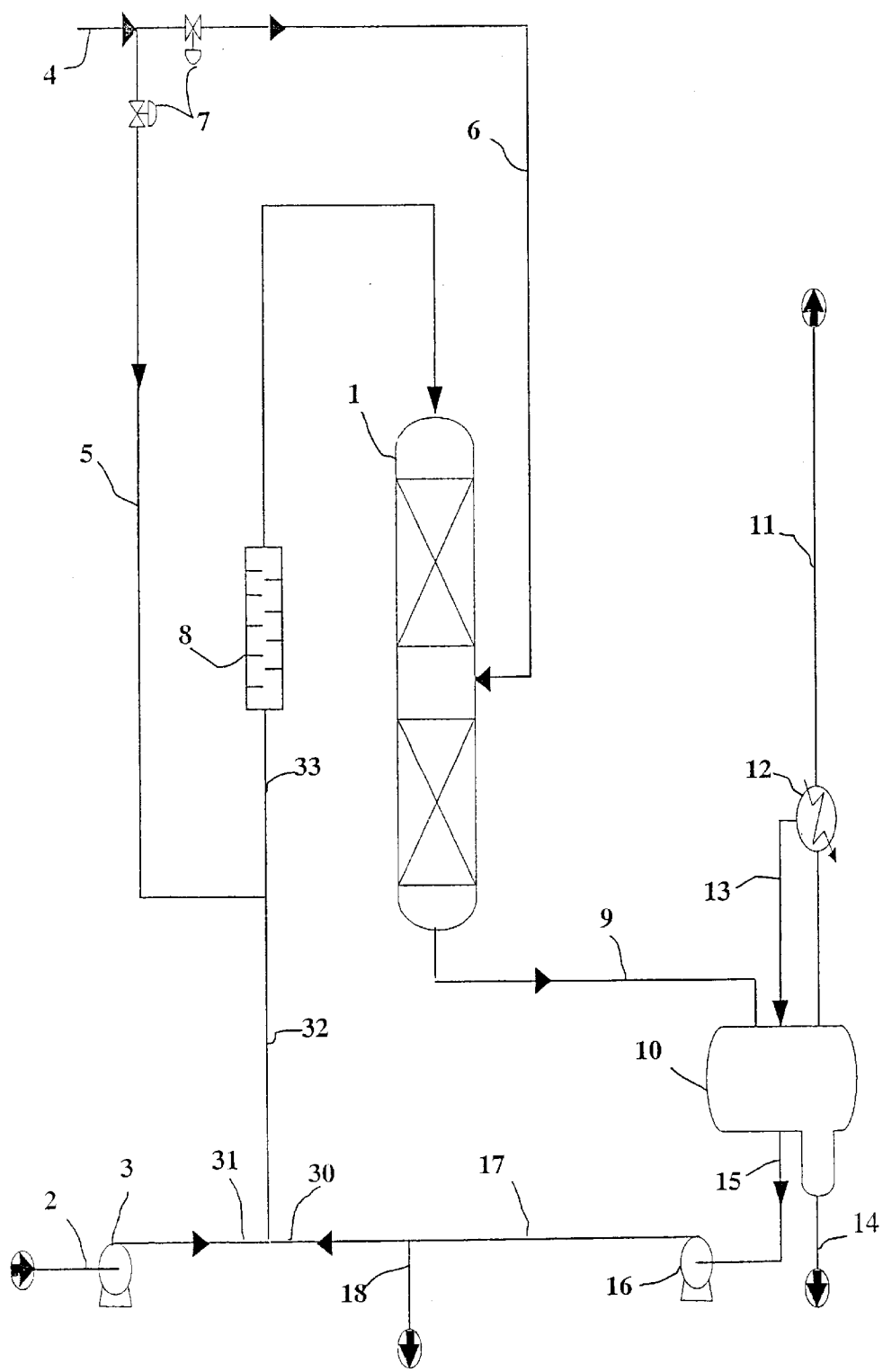

Partial hydrogenation of a butadiene-rich C4 petroleum cut. The compositions of the feed to be treated, the liquid phase at the reactor inlet and the product are shown in Table 1. The catalyst contained 0.2% by weight of palladium on a high purity alumina support for both beds in the reactor; the specific surface area of the catalyst was 70 m$^2$/g. The reaction scheme corresponded to the flowchart of FIG. 2. The pressure at the reactor inlet was 1.3 MPa; the temperature was 43° C. The ratio of the recycle mass flow rate to the feed mass flow rate was 17. The hourly space velocity, corresponding to the ratio of the feed volume flow rate at 15° C. to the volume of catalyst, was 4 h$^{-1}$ (m$^3$/m$^3$ catalyst/h). The distribution of the gas feed between the inlet and the middle of the reactor was 50% for the inlet and 50% for the intermediate level. The proportion of hydrogen in the gas feed was 99.8 mole %. The selectivity η for butenes with respect to butadiene was 87.8%. The butadiene content at the outlet was 0.29% by weight. The butadiene conversion in the reactor was 90.2%.

TABLE 1

Composition of feed, of flow at reactor inlet and of product in Example 1

| Components | Feed % by weight | Reactor inlet % by weight | Product % by weight |
| --- | --- | --- | --- |
| 1,3-butadiene | 45.20 | 2.96 | 0.29 |
| 1,2-butadiene | <0.1 | <0.1 | <0.1 |
| Vinyl acetylene | 1.64 | 0.10 | <0.1 |
| Ethyl acetylene | <0.1 | <0.1 | <0.1 |
| Isobutene | 20.79 | 21.10 | 21.12 |
| 1-butene | 13.59 | 16.92 | 17.13 |
| Cis-2-butene | 3.99 | 14.63 | 15.30 |
| Trans-2-butene | 6.14 | 33.07 | 34.77 |
| Isobutane | 4.51 | 4.74 | 4.75 |
| n-butane | 4.13 | 6.48 | 6.63 |

EXAMPLE 2

Figure 4:
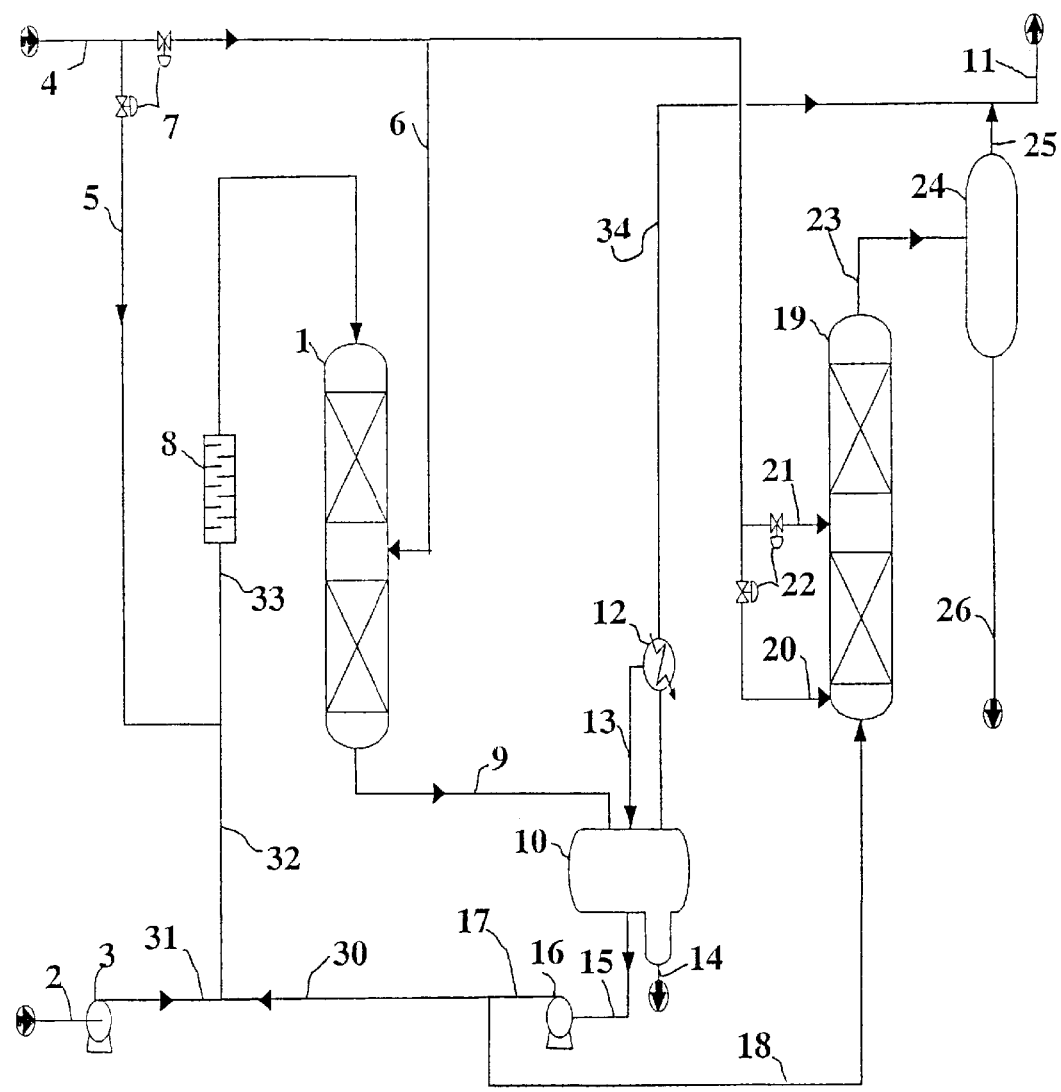

Hydrogenation of a butadiene-rich petroleum cut. The compositions of the feed to be treated, the flow at the reactor inlet and the product from reactor (1) are shown in Table 2. The reaction scheme corresponded to that of FIG. 4. The catalyst contained 0.2% by weight of palladium on a high purity alumina support for the two beds in the first reactor and 0.3% by weight of palladium on a high purity alumina support for the two beds of the second reactor. The specific surface area of the catalyst was 70 m$^2$/g. The pressure at reactor (1) inlet was 2.41 NPa and the temperature was 40° C. The ratio of the mass flow rate of the recycle to the feed mass flow rate of the feed to be treated was 22. The hourly space velocity corresponded to the ratio of the feed flow rate at 15° C. to the volume of catalyst, and was 3.8 h$^{-1}$ (m$^3$/m$^3$ catalyst/h). The distribution of the gas feed between the inlet and the middle of the reactor was 55% for the inlet and 45% for the middle of the reactor. The concentration of hydrogen in the gas feed was 93 mole %, the remainder being methane. The butene selectivity η with respect to butadiene transformed for reactor (1) was 98.4% and the percentage of butadiene at the outlet from reactor (1) was 1.3% by weight.

At the inlet to reactor (19), the pressure was 2.6 MPa and the temperature was 35° C. The composition of the liquid flow at the inlet and the product from reactor (19) are shown in Table 3. The distribution of the gaseous feed between the inlet and the middle of the reactor was 60% at the inlet and 40% at the middle. The hourly space velocity, corresponding to the ratio of the feed flow rate at 15° C. to the volume of catalyst, was 6 h$^{-1}$. The discharge gas contained 42% by weight of methane and 51% by weight of butenes. The selectivity for butenes with respect to the total butadiene transformed in the two reactors was 97%. The butadiene content at the outlet from reactor (19) was less than 100 ppm. The butadiene conversion over the whole scheme was 100%.

TABLE 2

Composition of the feed, of flow at inlet and of product from reactor (1) in Example 2

| Constituent | Feed % by weight | Reactor 1 inlet % by weight | Product % by weight |
| --- | --- | --- | --- |
| 1,3-butadiene | 48.53 | 3.07 | 0.98 |
| 1,2-butadiene | 0.16 | 0.02 | 0.01 |
| Vinyl acetylene | 0.61 | 0.03 | <0.01 |
| Ethyl acetylene | 0.15 | 0.01 | <00.1 |
| Isobutene | 24.54 | 24.93 | 24.95 |
| 1-butene | 12.91 | 39.41 | 40.63 |
| Cis-2-butene | 3.95 | 7.45 | 7.61 |
| Trans-2-butene | 5.15 | 20.39 | 21.09 |
| Isobutane | 0.61 | 0.65 | 0.65 |
| n-butane | 3.39 | 4.06 | 4.09 |

TABLE 3

Composition of flow at inlet and of product from reactor (19) in Example 2

| Constituent | Reactor 2 inlet % by weight | Product % by weight |
| --- | --- | --- |
| 1,3-butadiene | 0.98 | <0.01 |
| 1,2-butadiene | 0.01 | <0.01 |
| Vinyl acetylene | <0.01 | <0.01 |
| Ethyl acetylene | <0.01 | <0.01 |
| Isobutene | 24.95 | 24.80 |
| 1-butene | 40.63 | 35.94 |
| Cis-2-butene | 7.61 | 9.35 |
| Trans-2-butene | 21.09 | 23.66 |
| Isobutane | 0.65 | 0.66 |
| n-butane | 4.09 | 5.60 |

What is claimed is:
1. A process for hydrogenating a liquid cut containing hydrocarbons, including unsaturated molecules containing at least two double bonds or at least one triple bond, which comprises:

partially hydrogenating the unsaturated molecules containing at least two double bonds or at least one triple bond into less unsaturated molecules containing at least one double bond, in at least one reactor comprising at least two distinct beds of at least one hydrogenation catalyst, wherein a portion of a gas phase containing hydrogen is introduced as a mixture with said cut upstream of the first catalyst bed and a portion thereof is introduced upstream of the subsequent beds contained in said reactor, wherein in the first reactor hydrogenation is carried out in a liquid and gas downflow mode and wherein a gas/liquid mixture from said first reactor is sent to a separation section from which a gas phase is recovered, an aqueous phase is eliminated and a liquid phase is recovered containing the hydrogenated product from said first reactor, at least a portion of which is returned as a mixture with said cut to the inlet to said first reactor upstream of the first catalyst bed contained in said first reactor, wherein the recycle ratio of the portion which is returned to the first reactor is from 10:1 to about 30:1, the recycle ratio being the ratio of the volume flow rate of the recycle to the volume flow rate of the liquid cut feed to said reactor.

2. A process according to claim 1, wherein hydrogenation is carried out with a flooded gas-liquid flow regime with a volume boil-off rate in the range 5% to 30%.

3. A process according to claim 1, wherein hydrogenation is carried out in liquid flow alone, with a boil-off rate in the range 0 to 5%.

4. A process according to claim 1, wherein the cut containing the hydrocarbons is a cut consisting essentially of hydrocarbons containing butadiene.

5. A process according to claim 1, wherein the cut contains butadiene in a proportion by weight of about 20% to about 95%.

6. A process according to claim 1, wherein the recycle ratio is about 15:1 to about 25:1.

7. A process according to claim 1, wherein the first reactor contains two successive beds of catalyst and the distribution of the flow rate of the hydrogen-containing gas phase injected as a mixture with the liquid cut into the head of the first reactor upstream of the first catalyst bed is about 50 mole % to about 70 mole % with respect to the total molar flow rate of the gas phase injected into the reactor.

8. A process according to claim 1, wherein upstream of said introduction into said reactor, the liquid feed and the gas phase introduced into the head of the first reactor traverse a static mixer.

9. A process according to claim 1, wherein hydrogenation is carried out in two successive reactors, the first operating in liquid and gas downflow mode and the second operating in liquid and gas upflow mode, containing:

at least two successive beds of catalyst;

introduction upstream of each of the catalyst beds of a gas phase containing hydrogen corresponding to a portion of the total gas phase introduced into said reactors;

introduction of a liquid phase corresponding to a portion of the hydrogenated product from said first reactor.

10. A process according to claim 9, wherein the second reactor contains two successive beds of catalyst and the flow rate of the gas phase containing hydrogen injected upstream of the first bed of catalyst is about 50% to about 70% with respect to the total molar flow rate of the gas phase injected into said reactor.

11. A process according to claim 1, wherein the gas phase from the separation section is sent to a chilling section from which a liquid phase is recovered that is recycled to the separation section.

12. A process according to claim 1, wherein the hydrogenation catalysts used are identical or different in each catalytic bed of each of the reactors and comprise at least one noble group VIII metal on a mineral support.

13. A process according to claim 12, wherein the first reactor comprises two identical beds of catalyst containing the same noble group VIII metal on the same mineral support in identical proportions.

14. A process according to claim 12, wherein the catalyst contains a doping agent selected from the group consisting of gold, silver and copper in a quantity of about 1 to about 10000 ppm by weight with respect to the support.

15. A process according to claim 1, wherein the gas phase introduced into the reactor or reactors contains 60 mole % to 99.99 mole % of hydrogen, the complement to 100% being an inert gas.

16. A process according to claim 9, wherein the proportion of noble metal contained in the catalyst used in the first reactor is less than that of the catalyst used in the second reactor.

17. A process according to claim 13, wherein the catalyst contains a doping agent selected from the group formed by gold, silver and copper in a quantity of about 1 to about 10000 ppm by weight with respect to the support.

18. A process according to claim 15, wherein the inert gas is methane, propane, butane, nitrogen, argon, carbon monoxide or carbon dioxide.

* * * * *